United States Patent [19]

Noishiki et al.

[11] Patent Number: 4,704,131
[45] Date of Patent: Nov. 3, 1987

[54] MEDICAL MATERIALS

[75] Inventors: Yasuharu Noishiki, Tottori; Teruo Miyata, Tokyo, both of Japan

[73] Assignee: Koken Co., Ltd., Tokyo, Japan

[21] Appl. No.: 661,258

[22] Filed: Oct. 15, 1984

Related U.S. Application Data

[63] Continuation-in-part of Ser. No. 486,231, Apr. 18, 1983, abandoned.

[30] Foreign Application Priority Data

Apr. 19, 1982 [JP] Japan ................................. 57-65054

[51] Int. Cl.⁴ ........................... A61F 2/04; A61F 2/06; A01N 1/02
[52] U.S. Cl. .......................................... 623/66; 623/1; 623/2; 623/3; 623/11; 623/12; 427/2; 424/95; 128/DIG. 8
[58] Field of Search ....................... 623/1, 2, 11, 66, 3, 623/12; 128/334 R, DIG. 8; 427/2; 424/95

[56] References Cited

U.S. PATENT DOCUMENTS 3,955,012  5/1976  Okamara ..................... 128/DIG. 8
4,175,182  11/1979  Schmer ............................ 424/183
4,321,711  3/1982  Mano ..................................... 623/1
4,453,939  6/1984  Zimmerman ........................ 604/368
4,510,084  4/1985  Eibl ..................................... 424/101

Primary Examiner—Richard J. Apley
Assistant Examiner—Alan W. Cannon
Attorney, Agent, or Firm—Armstrong, Nikaido, Marmelstein & Kubovcik

[57] ABSTRACT

The medical material contains heparinized collagen in which heparin has been bonded to protamine covalently fixed on collagen, and, owing to its excellent compatibility with living bodies, especially, its superb antithrombotic property, can be suitably used as a substituent material for tissues or organs which are brought into direct contact with blood, namely, as aritificial vessels, artificial valves and patching materials for cardiovascular organs, and the above medical material is also suitable as a membrane having anti-adhesion effects. The medical material is obtained by immersing and treating a natural or artificial material successively in an aqueous protamine solution, an aqueous glutaraldehyde solution and an aqueous heparin solution.

8 Claims, 1 Drawing Figure

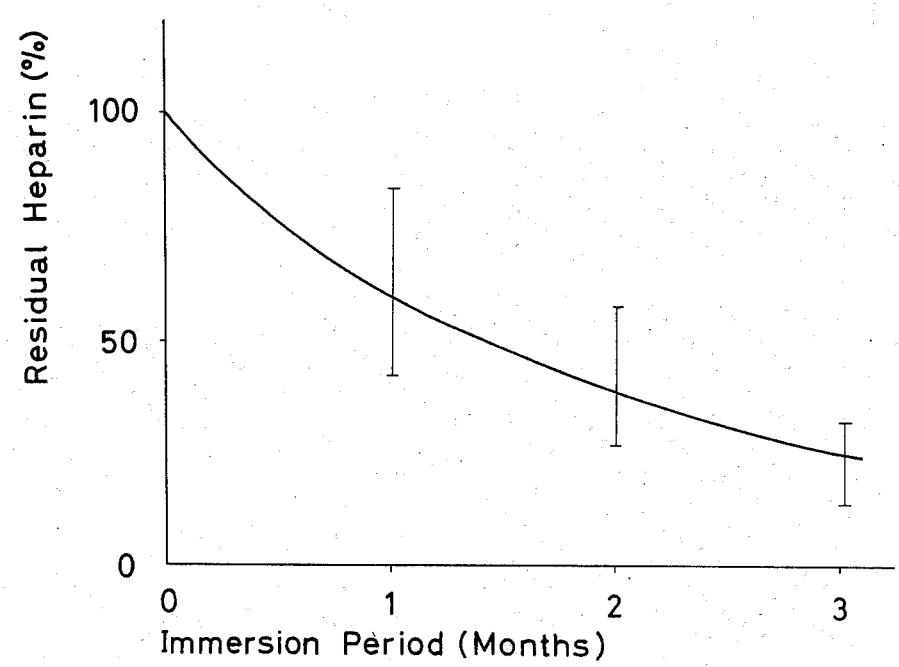

MEDICAL MATERIALS

CROSS-REFERENCE TO RELATED APPLICATION

This application is a Continuation-In-Part of application Ser. No. 486,231, filed Apr. 18, 1983, now abandoned entitled "Medical Materials".

BACKGROUND OF THE INVENTION (1) Field of the Invention

This invention relates to medical materials having excellent compatibility with living bodies, especially, a superb antithrombotic property and to their production process.

(2) Brief Description of the Prior Art

Medical materials used in direct contact with blood, such as artificial vessels and artificial heart valves, encounter the extremely serious problem of thrombus development.

Materials containing collagen, such as animal carotid arteries and human umbilical veins, have been conventionally used as artificial vessel materials. In artificial vessels making use of such materials, it has been known that they are susceptible to developing thrombi and are thus often obstructed in the initial stages of their use. Namely, when blood is brought into contact with surfaces of such artificial vessels which surfaces are formed of foreign bodies other than endothelial cells, the blood immediately forms thrombi. It is thus most important for successful blood-contacting organs such as artificial vessels, artificial valves and artificial hearts to suppress the thrombus formation and, if possible, to achieve the formation of pseudoendotheliums.

A variety of intensive research have been carried out to suppress thrombus formation. Under the circumstances, no ideal antithrombotic medical materials have yet been developed.

OBJECTS AND SUMMARY OF THE INVENTION

Accordingly, the present inventors contemplated that collagen-containing materials such as those described above would be extremely effective for use in artificial vessels if they would be rendered antithrombotic by stably heparinizing them with heparin (an acidic polysaccharide) which has a blood coagulation inhibitory effect. The present inventors have now found that the heparinized collagen, which has been formed by fixing protamine, a strongly basic protein, on collagen and then bonding heparin to the protamine, can be used as a medical material having excellent antithrombotic property.

An object of this invention is to provide a medical material which, when applied to an artificial vessel, exhibits an excellent antithrombotic property.

Another object of this invention is to provide a medical material which is useful as a membrane having an anti-adhesion effect.

A further object of this invention is to provide a production process for the above-described medical materials.

The above and other objects of this invention will become apparent from the following description of the present invention.

BRIEF DESCRIPTION OF THE DRAWING

The accompanying sole drawing shows the relationship between immersion period and residual heparin(%) when an artificial vessel according to one embodiment of this invention was immersed in a physiological saline.

DESCRIPTION OF THE PREFERRED EMBODIMENTS

One example of the medical material according to this invention is the one formed by covering a base, which is made of such a synthetic polymer as described below, with collagen which has been heparinized via protamine as will be described below. As the synthetic polymer may be mentioned polyesters such as polyethylene terephthalates. When a base made of such a synthetic polymer is kept inserted subcutaneously in an animal, the connective tissue (consisting principally of collagen) of the animal adheres around the base. Thus, by forming the above-described base of a tube of polyester mesh, the polyester mesh tube bearing a tubular connective tissue thereon is obtained. It may be used as a starting artificial material for medical materials according to this invention.

Among starting materials useful in the practice of this invention may be mentioned tissues and organs making up living bodies, for example, animal carotid arteries, ureters, umbilical veins, pericardia and connective tissue pipes and natural materials derived from human tissues, as well as artificial materials containing collagen such as collagen tubes, collagen membranes, collagen sponges, nonwoven collagen fabrics and collagen yarns.

The heparinization of collagen may be carried out in the following manner. First of all, one of the above-described collagen-containing natural and artificial materials is immersed in an aqueous protamine solution so as to impregnate collagen fibers with protamine. After dipping the thus protamine-impregnated material in an aqueous glutaraldehyde solution, it is immersed in an aqueous heparin solution to provide a medical material containing heparinized collagen.

The above-mentioned aqueous protamine solution may be an aqueous solution of protamine sulfate or other protamine salts. The concentration of protamine in such an aqueous solution may range from 0.0001 wt. % to its saturation, and preferably 1 wt. % to its saturation. The immersion in this aqueous solution is carried out at a temperature in the range of 0°–50° C. for 1–60 minutes, and preferably 5°–50° C. for 1–10 minutes.

The dipping in the aqueous glutaraldehyde solution is effected at a temperature in the range of 0°–50° C. for 1–60 minutes, and preferably 5°–50° C. for 1–20 minutes, using an aqueous solution which contains 0.001–5 wt. %, and preferably 0.1–5 wt. %, of glutaraldehyde.

On the other hand, the concentration of the aqueous heparin solution may range from 0.0001 wt. % to 10 wt. %, preferably 0.01–10 wt. %, and more preferably 0.5 wt. % to 3 wt. %. The immersion in the aqueous heparin solution is carried out at a temperature in the range of 0°–50° C., and preferably 5°–50° C., at pH 2–10, and preferably at pH 4–8, for 1 minute–3 days, and preferably 1 day–3 days.

Following the above procedures, it is ensured that a sufficient amount of heparin is bonded to protamine. In other words, a bond is formed between a positively-charged protamine and a negatively-charged heparin. Free heparin, which is not bonded to protamine, is removed by washing the heparin-treated material with water for 3 days.

It has been found through in vitro tests that medical materials containing the thus-heparinized collagen exhibit a low release rate of heparin in physiological saline and they permit the release of heparin over a long period of time. Therefore, such medical materials may be used as artificial organs which are brought into contact with blood, for example, artificial vessels, artificial valves and patching materials for cardiovascular organs. As a result of experiments using dogs, it has been found that such medical materials do not develop thrombi over a long period of time from the initial stage of their implantation and exhibit a stable antithrombotic property. It has also been found that medical materials containing collagen heparinized in such a manner as described above are effective as anti-adhesion membranes.

The present invention will be described in detail by the following examples.

EXAMPLE 1

A tube of 7 mm in inner diameter and 5.7 cm in length was formed of a Tetoron mesh (Tetoron: trade-mark for polyester fibers manufactured by Toray Industries, Inc., Japan). The tube was kept inserted subcutaneously for 20 days in an adult dog and then taken out as a connective tissue tube together with connective tissues attached around the mesh. The connective tissue tube was then treated overnight with a phosphate buffer (pH 7.0) which contained 0.01% of ficin. After washing the thus-treated tube with a physiological saline, it was immersed in an aqueous solution of protamine sulfate (concentration of protamine: 3%) for 1 minute. It was further dipped for 5 minutes in a 1% aqueous solution of glutaraldehyde to fix the protamine. After heparinizing the tube by immersing the same in an aqueous solution of heparin (concentration: 1%, pH 6) at 50° C. for 2 days, the resulting heparinized tube was washed with water for 3 days while changing the water 3 to 5 times a day. The heparinized connective tissue tube was then employed as an artificial vessel for a part of the thoracic descending aorta of a dog. No thrombus adhered at all to the artificial vessel from the very beginning and the artificial vessel did not develop any obstruction and remained as a stable and antithrombotic artificial vessel over a long period of time.

EXAMPLE 2

Surrounding fatty tissue was removed from a pig ureter. The resulting ureter was immersed overnight in a phosphate buffer (pH 7.0) containing 0.01% of ficin. Subsequent to washing the ureter with water, it was dipped in an aqueous solution of protamine sulfate (concentration of protamine: 5%) for 3 minutes. It was then dipped in a 1% aqueous solution of glutaraldehyde for 5 minutes to fix the protamine. After heparinizing the ureter by immersing the same in an aqueous solution of heparin (concentration: 1%, pH: adjusted to pH 6 with acetic acid) at 50° C. for 2 days, the resulting heparinized ureter was washed with water for 3 days while changing the water 3–5 times a day.

The heparinized pig ureter was then cut into a 5 cm-long sample. The sample was immersed in 1 liter of a physiological saline maintained at room temperature. The physiological saline was changed once every week and the amount of heparin in the sample was measured over a period of time. The quantitative analysis of heparin was carried out by measuring the sulfur in the heparin by means of an X-ray microanalyzer. In the graph of the drawing, the ratios of the measured heparin quantities to the initial heparin quantity are plotted as residual heparin (%) against their corresponding immersion periods. As readily envisaged from the graph, the heparinized pig ureter of this Example retained as much as about 25% of the initial heparin even after 3 months of immersion. Thus, it is understood that the release rate of heparin is low and the heparinized pig ureter has a long-lasting antithrombotic effect.

The heparinized pig ureter obtained in this Example was used as an artificial vessel for a part of the thoracic descending aorta of a dog. This artificial vessel did not develop any thrombus from the beginning and exhibited a stable antithrombotic property over a long period of time.

EXAMPLE 3

A pig ureter prepared similarly to Example 2 was dipped in an aqueous solution of protamine sulfate (concentration of protamine: 0.005%) for 20 minutes. It was then dipped in a 0.05% aqueous solution of glutaraldehyde for 25 minutes to fix the protamine. After heparinizing the ureter by immersing the same in an aqueous solution of heparine (concentration: 0.005%, pH: adjusted to pH 6 with acetic acid) at 3° C. for 10 hours, the resulting heparinized ureter was washed with water for 3 days while changing the water 3–5 times a day.

This heparinized pig ureter was cut into a 5 cm-long sample. The sample was immersed in 1 liter of a physiological saline maintained at room temperature. The physiological saline was changed once every week and the amount of heparin in the sample was measured over a period of time. The quantitative analysis of heparin was carried out by measuring the sulfur in heparin by means of an X-ray micro-analyzer. It was thereby demonstrated that the release rate of heparin was low.

The heparinized pig ureter obtained in this Example was used as an artificial vessel for a part of the thoracic descending aorta of a dog. This artificial vessel did not develop any thrombus from the beginning and exhibited a stable antithromobitc property over a long period of time.

What is claimed is:

1. A medical material containing heparinized collagen in which heparin has been ionically bonded to protamine covalently fixed on said collagen.

2. A medical material according to claim 1, which comprises a base structure of synthetic polymer covered with one material selected from the group of collagen and connective tissue, said collagen and said connective tissue having been heparinized by ionically bonding heparin to protamine covalently fixed to said collagen and said connective tissue.

3. A medical material according to claim 2, wherein said base structure is a tube formed of a polyester mesh.

4. A medical material according to claim 1, which is in the form of a natural tissue tube or natural tissue membrane derived from a living body, said collagen of said natural tissue tube or said membrane having been heparinized by bonding heparin to protamine covalently fixed to said collagen.

5. A medical material according to claim 1, which has been formed of an artificial material which contains said collagen heparinized by ionically bonding heparin to protamine covalently fixed to said collagen.

6. A medical material according to claim 1, wherein the protamine fixation to said collagen has been performed by impregnating collagen with protamine and by covalently fixing protamine to collagen with glutaraldehyde.

7. A medical material according to claim 2, wherein said connective tissue has been formed on the base structure of synthetic polymer by subcutaneously implanting said base structure of synthetic polymer into an animal.

8. A medical material according to claim 4, wherein said natural tissue tube is a ureter or a blood vessel.

* * * * *